(12) United States Patent
Jackstell et al.

(10) Patent No.: US 7,504,542 B2
(45) Date of Patent: Mar. 17, 2009

(54) PREPARATION OF α-HYDROXY KETONES VIA CARBENE-CATALYZED UMPOLUNG REACTION OF ALDEHYDES

(75) Inventors: Ralf Jackstell, Cuxhaven (DE); Irina Jovel, Rostock (DE); Matthias Beller, Ob Nienhagen (DE); Martin Hateley, Aschaffenburg (DE); Christoph Weckbecker, Gründau-Lieblos (DE); Klaus Huthmacher, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 11/889,304

(22) Filed: Aug. 10, 2007

(65) Prior Publication Data

US 2008/0051608 A1 Feb. 28, 2008

(30) Foreign Application Priority Data

Aug. 18, 2006 (DE) ........................ 10 2006 038 934

(51) Int. Cl.
*C07C 45/72* (2006.01)
*C07C 319/00* (2006.01)
*C07D 233/00* (2006.01)

(52) U.S. Cl. ............................ 568/388; 568/41; 568/42; 548/352.1

(58) Field of Classification Search .................... 568/41, 568/42, 388; 548/352.1
See application file for complete search history.

(56) References Cited

U.S. PATENT DOCUMENTS 5,298,668 A 3/1994 Gehrer et al.

FOREIGN PATENT DOCUMENTS

WO WO-2005/113626 12/2005
WO WO 2008/038810 A1 * 4/2008

OTHER PUBLICATIONS

Tudose et al. Imidazol(in)ium-2-carboxylates as N-heterocyclic carbene precursors in ruthenium-arene catalysts for olefin metathesis and cyclopropanation. Journal of Organometallic Chemistry, 2006, vol. 691, pp. 5356-5365.*

Tudose et al. Imidazol(in)ium carboxylates as N-heterocyclic carbene ligand precursors for Suzuki-Miyaura reactions. Tetrahedron Letters, 2006, vol. 47, pp. 8529-8533.*
International Search Report for PCT/EP2007/057626.
Written Opinion of the International Searching Authority for PCT/EP2007/057626.
Duong, et al., "Reversible Carboxylation of N-Heterocyclic Carbenes," *Chem. Commun.* 112-113 (2004).
Schössler, et al., "Stabile Dipole aus 1,1',3,3'-Tetraphenyl-2,2'-biimidazolidinyliden und Acyliso- bzw. Acylisothiocyanaten," *Chem. Ber.* 107:1931-1948 (1974).
Tommasi, et al., "Synthesis of 1,3-dialkylimidazolium-2-carboxylates by Direct Carboxylation of 1,3-diakylimidazolium Chlorides with $CO_2$," *Tetrahedron Letters* 47:6453-6456 (2006).
Breslow, et al., "On the Mechanism of Thiamine Action. IV. Evidence from Studies on Model Systems," *J. Am. Chem. Soc.* 80 3719-3726 (1958).
Castells, et al., "Use of Thiazolium-2-Carboxylates to Induce Benzoin Condensations," *Tetrahedron Letters* 26:5457-5456 (1985).
Nyce, et al., "In Situ Generation of Carbenes: A General and Versatile Platform for Organocatalytic Living Polymerization," *J. Am. Chem. Soc.* 125:3046-3056 (2003).

* cited by examiner

*Primary Examiner*—Sikarl A Witherspoon
(74) *Attorney, Agent, or Firm*—Michael A. Sanzo; Law Office of Michael A. Sanzo, LLC

(57) ABSTRACT

The present invention relates to the preparation of α-hydroxy ketones of the general formula I. In particular, the invention relates to novel imidazolinium carboxylate adducts and to a novel process for using catalytic amounts of imidazolium and imidazolinium carboxylate adducts in the acyloin reaction of aldehydes to prepare hydroxy ketones of the general formula I,

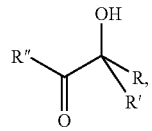

Formula I where R and R' are the same or different and are each H or a straight-chain or branched and optionally substituted $C_1$-$C_{12}$-alkyl radical, and R"=$H_3CSCH_2CH_2$, t-butyl, n-butyl, sec-butyl, n-propyl, i-propyl, an optionally heteroatom-substituted $C_6$-$C_{18}$-aryl, heteroaryl, $C_6$-$C_{18}$-arylalkyl, especially phenylmethyl, where phenyl may again be heteroatom-substituted, or heteroalkyl.

20 Claims, No Drawings

PREPARATION OF α-HYDROXY KETONES VIA CARBENE-CATALYZED UMPOLUNG REACTION OF ALDEHYDES

CROSS REFERENCE TO RELATED APPLICATIONS

The present application claims priority to German application 10 2006 038 934.4, filed on Aug. 18, 2006, which is incorporated in its entirety herein by reference.

FIELD OF THE INVENTION

The present invention relates to the preparation of α-hydroxy ketones of the general formula I and, in the case when R'=R=H, their subsequent oxidation to α-keto acids.

In particular, the present invention relates to novel imidazolinium carboxylate adducts and to a novel process for using catalytic amounts of imidazolium and imidazolinium carboxylate adducts in the acyloin reaction (umpolung reaction of aldehydes) to prepare hydroxy ketones of the general formula I,

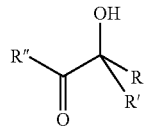

Formula I where R and R' are the same or different and are each H or a straight-chain or branched and optionally substituted C1-C12-alkyl radical, and R"=H3CSCH2CH2, t-butyl, n-butyl, sec-butyl, n-propyl, i-propyl, an optionally heteroatom-substituted C6-C18-aryl, heteroaryl, C6-C18-arylalkyl, especially phenylmethyl, where phenyl may again be heteroatom-substituted, or heteroalkyl.

BACKGROUND OF THE INVENTION

Owing to their functionality, α-hydroxy ketones are important synthetic units for a multitude of chemicals, for example:

- for the preparation of heterocycles such as imidazoles (EP-A 252162) and imidazolones (Journal of the Chemical Society Perkin II 1981, 310), the precursors for active medicament and crop protectant ingredients,
- as a reducing agent in dyeing for the dyeing of textiles owing to their reduction capacity (EP-A 364752),
- as an aroma in foods, such as acetoin or the diacetyl resulting therefrom,
- and they are additionally important as a structural motif and frequent constituent in natural products, which might be of great significance for future medicaments (Journal of the American Chemical Society, 2004, 3070).

α-Keto acids can be prepared from α-hydroxy ketones of the general formula I where R'=R=H by a suitable oxidation of the alcohol functionality. The uses of α-keto acids include those as pharmaceutical products and precursors.

In addition, it would be possible to prepare the keto acid precursors of the important methionine or methionine hydroxy analogue (MHA) products by a suitable oxidation of the α-hydroxy ketones of the general formula I where R'=R=H and R"=CH3S(CH2)2. The crucial advantage would be that the highly toxic and dangerous hydrocyanic acid (HCN) used to date could be replaced by the much less dangerous formaldehyde (HCHO).

It is known to those skilled in the art that α-hydroxy ketones of the general formula I

Formula I can be prepared in various ways, for example by:

1. Benzoin reaction: this is understood to mean the addition of two aldehydes to an α-hydroxy ketone by an umpolung of an aldehyde with cyanide as a catalyst. Owing to the stabilization by the aromatic ring, the reaction with cyanide is restricted to aromatic aldehydes (Organische Chemie [Organic Chemistry], K. Peter C. Vollhardt VCH, 1. Auflage, 1988 p. 1025, and also Castells et al. Tetrahedron Letters 1985, 26, 5457). Thiazolium carbene-catalysed benzoin condensation has also been known for some time (Breslow, Journal of the American Chemical Society 1959, 3719).

2. Stetter reaction: this is understood to mean the addition of a reversed-polarity aldehyde with a 1,4-electrophile, which can be catalysed with carbene.

Known carbene catalysts are various N-heterocyclic carbenes which are useable in various ways—for example as ligands for transition metals, as nucleophilic catalysts for acylations, transesterifications or ring-opening polymerizations. The carbene catalyst classes used for umpolung of aldehydes are the thiazolium carbenes known from nature, the imidazolium carbenes and the triazolium carbenes.

The active carbene catalysts are normally sensitive towards water and air. They are obtained from the corresponding imidazolium, thiazolium or triazolium salt by deprotonation with a base. The bases used include sodium hydride, potassium hydride or potassium tert-butoxide in THF (Nair et al., Angewandte Chemie, 2004, Vol. 116, 5240 ff.).

However, it is also known that catalytic amounts of the active catalysts can be obtained in situ by the use of a biphasic system (Waymouth et al., Journal of the American Chemical Society, 2003, 3046).

3. Carbene-carboxylate/CO2 adducts: the CO2 adducts of the imidazolium or imidazolinium carbenes 1-7 which are listed in Table 1 are known.

TABLE 1

Known CO$_2$ adducts of imidazolinium and imidazolium salts

| Structure (Compound No.) | Name | Lit. |
| --- | --- | --- |
| 1 | 1,3-Diphenylimidazolinium-2-carboxylate | W. Schössler, M. Regitz. Chem. Ber. 1974, 107, 1931-1948. |
| 2 | 1,3-Diisopropyl-4,5-dimethyl-1H-imidazol-3-ium-2-carboxylate | N. Kuhn, T. Kratz. Synthesis 1993, 561-562. N. Kuhn, M. Steimann, G. Weyers. Z. Naturforsch. 1999, 54b, 427-433. |
| 3 | 1,3-Di-tert-butylimidazolium-2-carboxylate | K. Ishiguro, K. Hirabayashi, T. Nojima, Y. Sawaki. Chem. Lett. 2002, 796-797. |
| 4 | 1,3-Dimethylimidazolium-2-carboxylate | J. D. Holbrey, W. M. Reichert, I. Tkatchenko, E. Bouajila, O. Walter, I. Tommasi, R. D. Rogers. Chem. Comm., 2003, 28-29. |
| 5 | 1,3-Dimesityl-1H-imidazol-3-ium-2-carboxylate | H. A. Duong, T. N. Tekavec, A. M. Arif, J. Louie. Chem. Comm., 2004, 112-113. |
| 6 IMes·CO$_2$ | 1,3-bis (2,6-Diisopropylphenyl)-1H-imidazol-3-ium-2-carboxylate | |

TABLE 1-continued

Known CO$_2$ adducts of imidazolinium and imidazolium salts

| Structure (Compound No.) | Name | Lit. |
|---|---|---|
| 7 | 3-Tert-butyl-1-methyl-1H-imidazol-3-ium-2-carboxylate | I. Tommasi, P. Sorrentino. Tetrahedron Letters, 46 (2005) 2141-2145. |

Compounds 5 and 6 have been used for the preparation of oligomeric and polymeric isocyanates, especially uretdiones and isocyanurates (WO 2005-113626). Further carboxylate adducts of the imidazolium and imidazolinium structure and possible catalytic uses are not known to date.

The disadvantages in the prior art of acyloin formation from aldehydes are as follows:

The use of bases in acyloin formation reactions, for example for the release of catalytically active imidazolium carbene, causes side reactions such as aldol condensation between aldehydes and leads to a reduction in the yield of desired α-hydroxy ketones (acyloin).

The bases used subsequently have to be removed from the product, which means additional work and can lead to difficulties in the achievement of high purities—as required, for example, for pharmaceutical products.

In addition, no universal synthesis scheme for crossed aldehyde-aldehyde additions is known to date, in which different aldehydes are reacted with one another (cf. Angewandte Chemie, 2004, 1348).

In order to use imidazolium carbene carboxylates II or imidazolinium carboxylates III as the source of the actually active imidazolium or imidazolinium carbene catalysts, a decarboxylation is first necessary.

The decarboxylation of such, for example, unsaturated, imidazolium carbene carboxylates proceeds, according to H. A. Duong et al. (cf. above), however, only at temperatures from 187° C., so that the release of the catalytically active carbene was to be expected only at such temperatures. This result would have dissuaded the person skilled in the art from seriously considering the imidazolium carbene carboxylates as catalysts in acyloin formation owing to the marked side reactions at such high temperatures in the acyloin formation reaction.

OBJECT OF THE INVENTION

It was an object of this invention to provide suitable catalysts for a process for preparing α-hydroxy ketones by means of acyloin reaction, in which the in situ use of bases is not necessary, and a corresponding process. In particular, it was an object of the invention to discover stable, easy-to-handle carbene catalysts and compounds which generate the active carbene catalysts, which enable an acyloin reaction in a simple manner and under mild conditions and in particular avoid the disadvantages of the prior art. It was a further object of the invention to find an improved process, especially for the synthesis of α-keto alcohols, α-keto aldehydes or α-keto acids as precursors in the synthesis for pharmaceuticals or for methionine or for methionine hydroxy analogue (MHA), which avoids the disadvantages of the prior art mentioned.

DESCRIPTION OF THE INVENTION

By using compounds of the general formulae II and III:

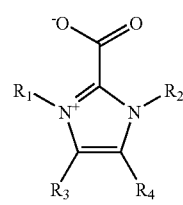

II

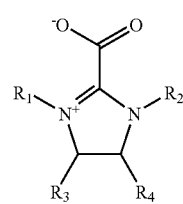

III as catalysts for the preparation of α-hydroxy ketones by means of acyloin addition of aldehydes, where $R_1$ and $R_2$ are the same or different and are each aryl, preferably $C_6$-$C_{10}$-aryl, heteroaryl, branched or unbranched alkyl, preferably $C_1$-$C_{10}$-alkyl, which is optionally mono- or poly-$C_1$-$C_4$-alkyl- or -heteroalkyl-substituted, $C_3$-$C_6$-cycloalkyl or mono- or poly-$C_1$-$C_4$-alkyl-substituted aryl, preferably mono- or poly-$C_1$-$C_4$-alkyl-substituted $C_6$-$C_{10}$-aryl, and $R_3$ and $R_4$ are the same or different and are each hydrogen, branched or unbranched $C_1$-$C_6$-alkyl, $C_3$-$C_6$-cycloalkyl, aryl, preferably $C_6$-$C_{10}$-aryl or heteroaryl, it is possible to overcome the disadvantages of the prior art.

Among the heteroaryl radicals, preference is given to pyridyl, quinolyl, isoquinolyl, imidazolyl, pyrrolyl and furyl radicals.

In particular, it is possible to completely avoid the presence of bases during the acyloin reaction.

As the Examples and Comparative Examples in Table 4 show, the use of the imidazolinium carbene carboxylate adducts as catalysts always leads to higher yields of acyloin product in comparison to the imidazolinium salts from which the active carbene catalysts are released only by the action of base.

The inventive use of the imidazolium and imidazolinium carbene carboxylates as catalysts apparently has the effect that elimination of $CO_2$ during the acyloin reaction always results in the presence of a sufficient amount of the actually catalytically active carbene species. This is possible in such an outstanding manner only by use of catalysts of the formula II or III. The presence of a saturated C—C bond between the two adjacent carbon atoms in the ring (imidazolinium structure III) in acyloin condensations with methylmercaptopropionaldehyde (MMP) appears to be of particular significance, since—as the inventors have found—comparably good results were not achievable with a corresponding unsaturated imidazolium compound of type II, as shown in particular by the comparison of Examples No. 31 and 32 (see Table 3).

In contrast to the decarboxylation of the unsaturated imidazolium carbene carboxylates which, according to H. A. Duong, takes place only from 187° C. (cf. above), it has been found here that, surprisingly, imidazolinium and imidazolium carbene carboxylates of the formula II and III decarboxylate sufficiently in the presence of aldehydes even at significantly lower temperatures of 0° C. to approx. 100° C. and generate an active carbene catalyst.

The inventive carbene carboxylates can therefore be used even at temperatures of −20° C. to 100° C. for the conversion of aldehydes to acyloins. However, this reaction is preferably performed at temperatures of 15° C. to approx. 80° C., more preferably at temperatures of 10 to 60° C., but most simply at room temperature.

The reaction is preferably conducted under a partial pressure of 0.1-20 bar of carbon dioxide.

The present invention therefore also provides compounds of the formula IV, which constitute a selection from the compounds of the formula III:

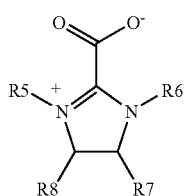
(IV)

where R5 and R6 are the same or different and are each $C_6$-$C_{10}$-aryl, mono- or poly-$C_1$-$C_4$-alkyl-substituted $C_6$-$C_{10}$-aryl, but preferably mesityl, optionally mono- or poly-$_1$-$C_4$-alkyl-substituted $C_1$-$C_{10}$-alkyl or $C_3$-$C_6$-cycloalkyl, and R7 and R8 are the same or different and are each hydrogen or branched or unbranched $C_1$-$C_6$-alkyl, preferably methyl, with the proviso that, when R7 and R8 are each hydrogen, R5 and R6 must not both be phenyl.

A particularly preferred compound is the compound $H_2IMes.CO_2$ where R5=R6=mesityl and R7=R8=hydrogen.

The present invention additionally provides for the use of compounds of the general formula IV as catalysts for the preparation of α-hydroxy ketones by means of the abovementioned acyloin addition.

The present invention also provides a process for preparing α-hydroxy ketones of the general formula I:

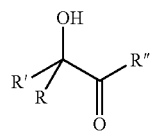
(I)

by reacting a carbonyl compound of the general formula RR'C=O with a carbonyl compound of the general formula HR''C=O, in the presence of an inventive catalyst of the general formulae II, III or IV (as defined above), where R and R' are the same or different and are each H or a straight-chain or branched and optionally substituted $C_1$-$C_{12}$-alkyl radical, and R''=$H_3CSCH_2CH_2$, t-butyl, n-butyl, sec-butyl, n-propyl, i-propyl, an optionally heteroatom-substituted $C_6$-$C_{18}$-aryl, heteroaryl, $C_6$-$C_{18}$-arylalkyl, especially phenylmethyl, where phenyl may again be heteroatom-substituted, or heteroalkyl.

In this context, heteroalkyl refers in particular to primary, secondary or tertiary amine radicals having a total of 1 to 12 carbon atoms, and ether or thioether groups having a total of 1 to 12 carbon atoms in each case, which are bonded via a carbon atom.

Preference is given to processes in which aldehydes where R=R'=H and
R''=$CH_3SCH_2CH_2$, i.e. $CH_2$=O and methylmercaptopropionaldehyde are used. These processes are outstandingly suitable for preparing precursors such as compound V for methionine or ketomethionine, or else for methionine hydroxy analogue (MHA), all of which find use in animal nutrition.

The necessary key reaction is the selective oxidation of the corresponding acyloin compound of the formula I to the keto acid (V), which can be used directly or can be converted to MHA or to methionine by simple reduction or reductive amination:

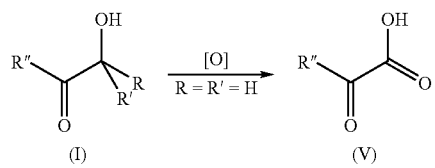

Preference is equally given to a process in which aldehydes where
R=H,
R'=$CH_3SCH_2CH_2$ and
R''=H are used, so as to form a compound with terminal aldehyde group and α-hydroxyl function (VII).

Whether compound VI or VII forms can in principle be influenced by a suitable selection of the reaction conditions. However, VI generally appears to be formed preferentially.

Preference is also given to a process in which aldehydes where
R=H
R'=$CH_3$ or $C_2H_5$ and
R''=$CH_3SCH_2CH_2$ find use.

In the aforementioned processes according to the invention, the imidazolium and imidazolinium carbene compounds (II) and (III) used as catalysts are used preferably in a concentration of 0.1-5 mol % based on that aldehyde which may be used in deficiency.

The solvents suitable in accordance with the invention for the acyloin formation reaction are $C_5$- to $C_8$-hydrocarbons, more preferably heptane, aromatic hydrocarbons, preferably toluene, benzene or xylene, or linear and cyclic ethers, preferably THF, diethyl ether and dioxane.

The present invention likewise provides the compounds of the formulae VI-VIII preparable in accordance with the invention.

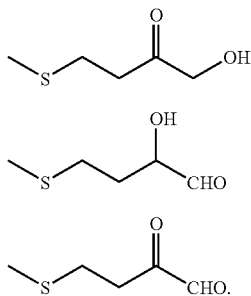

These compounds are valuable precursors, especially for the preparation of methionine or methionine replacements such as MHA for the animal feeds industry.

The present invention likewise provides a process for preparing catalysts of the general formulae II, III or IV

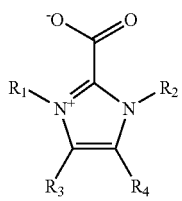

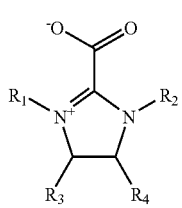

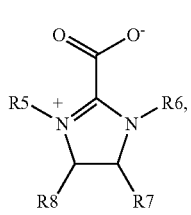

which is characterized in that a compound of the general formula IX, X or XI

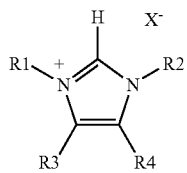

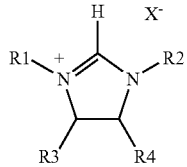

is reacted with $CO_2$ in the presence of a base, where X=Cl, Br, I, $pCH_3C_6H_4SO_3$, $BF_4$, $PF_6$, $CH_3SO_3$.

The bases used are preferably compounds whose corresponding acid has a pKa>8. Preference is given to using alkali metal and alkaline earth metal carboxylates, more preferably sodium acetate, alkali metal and alkaline earth metal alkoxides, more preferably potassium tert-butoxide, alkali metal and alkaline earth metal carbonates or primary, secondary or tertiary amines and bicyclic amines, preferably 1,8-diazabicyclo[5.4.0]undec-7-ene (DBU).

The reaction is performed generally at temperatures of −20° C. to 100° C. However, this reaction is performed preferably at temperatures of 15° C. to approx. 80° C., more preferably at temperatures of 10 to 60° C., but most simply at room temperature.

Preferred solvents are THF, diethyl ether or toluene.

The isolation and purification of the inventive imidazolinium carbene carboxylates can advantageously be accomplished by crystallization from alcohols.

Important advantages of the present invention are:
Fewer by-products are formed through dispensing with the use of base during the acyloin formation. The undesired aldol condensation is virtually completely prevented.
No additional assistants, such as said bases, need be used, and there is no need to remove them after the reaction.
A higher purity of the acyloin products is achieved in comparison to conventional processes.
The process according to the invention is notable for very favourable process conditions, such as low temperatures and low catalyst use.
The process according to the invention makes available some new important compounds for the animal feed additive industry. These can be produced in an economically viable manner and in good yields.

EXAMPLES AND COMPARATIVE EXAMPLES*

General Experimental Description Based on Examples 1-44

Paraformaldehyde and catalyst were weighed into an inert Schlenk flask, and the solvent (absolute tetra-hydrofuran, THF) was added. Subsequently, the reactant (aldehyde), the standard for GC analysis (toluene, 0.1 equiv. relative to the reactant) and, if appropriate, a base (in the case of use of the imidazolinium salts as carbene catalyst precursor=Comparative Examples) were added through a septum. The reaction mixture was stirred by means of magnetic stirring for approx. 30 min. The reaction was performed at room temperature (20-22° C.) within the reaction time specified in each case in Table 2-4. Once the reaction had ended (monitoring of the conversion by GC-FID), the product was purified by column chromatography after distillative removal of the solvent. All product structures shown below were confirmed by GC-MS and NMR data. The conversions (and yield) were determined by a separate calibration with reactants and previously isolated products. The differences between conversion and yields are for the most part attributable to di-, tri- and polymerized compounds as by-products.

TABLE 2

Experiments performed with 3-methylthiopropionaldehyde (MMP) in the presence of various catalysts

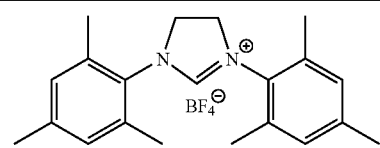

| Example | Catalyst | Conversion of MMP, % | Main product | Yield (Y) (GC, %) |
|---|---|---|---|---|
| 1*) | 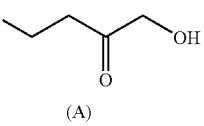 | 93 | Acyloin condensation | 50 |
| 2*) | 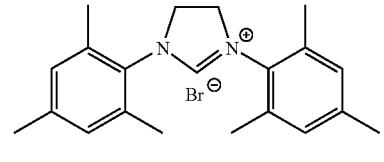 | 93 | 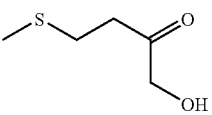 | 57 |
| 3*) | 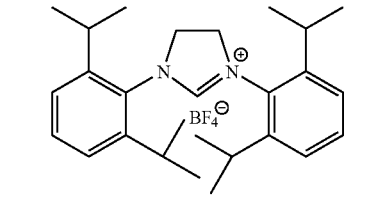 | 86 | | 44 |
| 4*) | 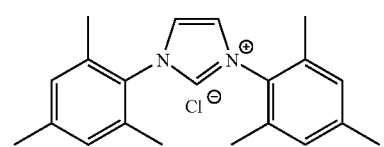 | 85 | Aldol condensation | 0 |
| 5*) | 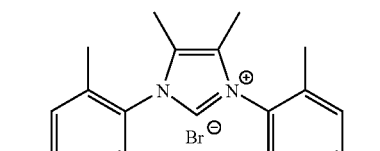 | 92 | 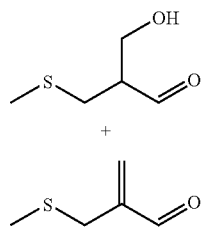 | 0 |
| 6*) | 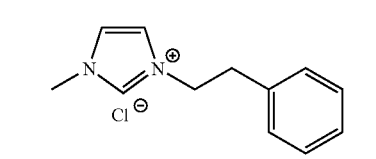 | 30 | | 0 |

TABLE 2-continued
Experiments performed with 3-methylthiopropionaldehyde (MMP) in the presence of various catalysts
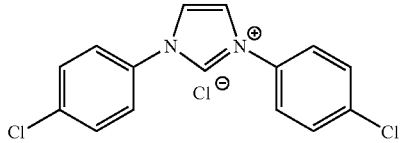
| Example | Catalyst | Conversion of MMP, % | Main product | Yield (Y) (GC, %) |
|---|---|---|---|---|
| 7*) | 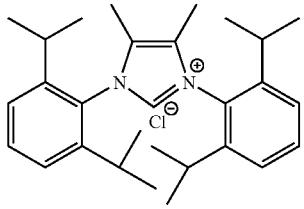 | 66 | | 0 |
| 8*) | 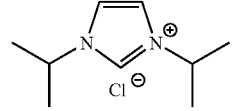 | 78 | | 0 |
| 9*) | 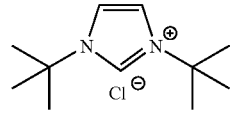 | 97 | | 0 |
| 10*) | 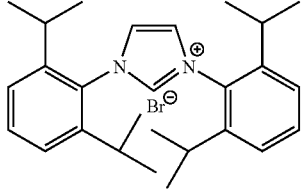 | 100 | | 0 |
| 11*) | 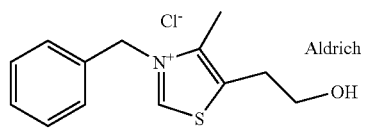 | 74 | | 0 |
| 12*) | 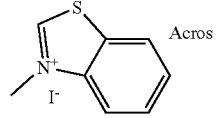 Aldrich | 67 | | 0 |
| 13*) |  Acros | 89 | | 0 |
*) = Comparative Example

TABLE 3

Experiments performed with 3-methylthiopropionaldehyde (MMP) under various conditions MMP + HCHO (paraform.) → (A) via THF abs., cat. base conc. of MMP in THF: 0.1 M

| Ex. | MMP (mmol) | H$_2$CO/MMP (mol) | Catalyst (mol %) | Base (base/cat., mol) | T [°C.] | t [h] | Conversion of MMP, % | Yield (A) (GC, %) |
|---|---|---|---|---|---|---|---|---|
| 14*) | 5 | 1 | H$_2$IMes•HBr (2) | Et$_3$N (10) | 60 | 16 | 50 | 48 |
|  |  |  |  |  |  | 18 | 52 | 46 |
| 15*) | 1 | 2 | (2) | DBU (8) | 60 | 4 | 86 | 44 |
| 16*) | 1 | 2 | H$_2$IMes•HBF$_4$ (2) | DBU (8) | 60 | 4 | 93 | 50 |
| 17*) | 1 | 2 | H$_2$IMes•HBr (2) | DBU (8) | 60 | 4 | 93 | 57 |
| 18*) | 1 | 2 | H$_2$IMes•HBF$_4$ (2) | DBU (8) | 50 | 4 | 93 | 70 |
| 19*) | 1 | 2 | H$_2$IMes•HBF$_4$ (2) | NaOAc (8) | 50 | 5 | 95 | 75 |
| 20*) | 1 | 1 | H$_2$IMes•HBF$_4$ (1) | DBU (8) | RT | 27 | 87 | 62 |
| 21*) | 1 | 1 | H$_2$IMes•HBF$_4$ (2) | DBU (8) | RT | 27 | 97 | 68 |
| 22*) | 2 | 2 | H$_2$IMes•HBF$_4$ (2) | DBU (8) | RT | 20 | 94 | 75 |
| 23*) | 20 | 2 | H$_2$IMes•HBF$_4$ (2) | DBU (8) | RT | 17 | 91 | 72 |
|  |  |  |  |  |  | 20 | 94 | 75 |
| 24*) | 1 | 2 | H$_2$IMes•HBF$_4$ (0.5) | DBU (8) | RT | 20 | 93 | 77 |
| 25*) | 1 | 2 | H$_2$IMes•HBF$_4$ (1) | DBU (8) | RT | 27 | 93 | 80 |
| 26*) | 1 | 2 | H$_2$IMes•HBF$_4$ (1) | DBU (8) | RT | 8 | 92 | 81 |
| 27 | 1 | 2 | H$_2$IMes•CO$_2$ (2) | no base | RT | 20 | 96 | 81 |
| 28 | 1 | 2 | H$_2$IMes•CO$_2$ (1) |  | RT | 8 | 96 | 92 |
|  |  |  |  |  |  | 22 | 97 | 93 |
| 29 | 1 | 2 | H$_2$IMes•CO$_2$ (0.7) |  | RT | 22 | 96 | 91 |
| 30 | 1 | 2 | H$_2$IMes•CO$_2$ (0.7) |  | RT | 22 | 90 | 90 |
| 31 | 1 | 2 | H$_2$IMes•CO$_2$ (0.3) |  | RT | 22 | 85 | 81 |
| 32 | 1 | 2 | IMes•CO$_2$ (1) |  | RT | 20 | 57 | 0 |

*) = Comparative Example

TABLE 4

Experiments performed with various aldehydes

R''CHO + HCHO (paraform) 2 eq → (THF abs., cat. 2 mol %, 60° C.)

conc. of R''CHO in THF: 0.1 M

| Ex. | Aldehyde | Catalyst | t [h] | Conversion of RCHO, % | Main product | Yield (GC, %) |
|---|---|---|---|---|---|---|
| 33*) | Pentanal | H₂IMes•HBF₄ + DBU (1:8 mol) | 20<br>44 | 69<br>72 | CH₃CH₂CH₂CH₂-C(O)-CH₂OH | 52<br>50 |
| 34 | | H₂IMes•CO₂ | 20<br>44 | 87<br>96 | | 67<br>70 |
| 35*) | Benz-aldehyde | H₂IMes•HBF₄ + DBU (1:8 mol) | 20<br>44 | 42<br>40 | Ph-C(O)-CH₂OH | 33<br>30 |
| 36 | | H₂IMes•CO₂ | 20<br>44 | 44<br>47 | | 35<br>35 |
| 37*) | Phenyl-propion-aldehyde | H₂IMes•HBF₄ + DBU (1:8 mol) | 20<br>44 | 90.5<br>92 | Ph-CH₂CH₂-C(O)-CH₂OH | 81<br>80 |
| 38 | | H₂IMes•CO₂ | 20<br>44 | 92<br>94 | | 80<br>81 |
| 39*) | Octanal | H₂IMes•HBF₄ + DBU (1:8 mol) | 20<br>44 | 65<br>68 | CH₃(CH₂)₅-C(O)-CH₂OH | 53<br>55 |
| 40 | | H₂IMes•CO₂ | 20<br>44 | 56<br>65 | | 48<br>55 |
| 41*) | Cyclohexane-aldehydes | H₂IMes•HBF₄ + DBU (1:8 mol) | 20<br>88 | 32<br>36 | Cyclohexyl-C(O)-CH₂OH | 26<br>30 |
| 42 | | H₂IMes•CO₂ | 20<br>44 | 33<br>40 | | 27<br>28 |
| 43*) | 5-Methyl-furfural (RT) | H₂IMes•HBF₄ + DBU (1:8 mol) | 20<br>44 | 67<br>71 | 5-methyl-2-furyl-C(O)-CH₂OH | 58<br>60 |
| 44 | | H₂IMes•CO₂ | 20<br>44 | 68<br>70 | | 58<br>62 |

*) = Comparative Example

Explanation for Tables 3, 4:

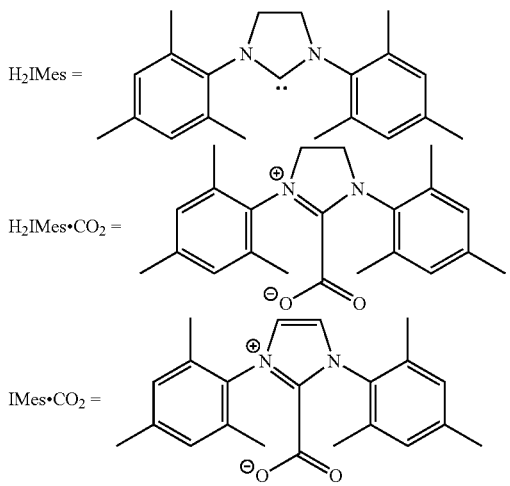

NMR and MS data of selected products:

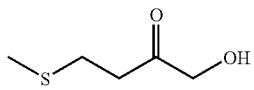

1-Hydroxy-4-(methylthio)butan-2-one $^1$H NMR (300 MHz, CDCl$_3$, 25° C.): δ=2.06 (s, 3H, CH$_3$), 2.06-2.82 (m, 4H, CH$_2$CH$_2$), 3.03 (bs, 1H, OH), 4.22 (s, 2H, CH$_2$OH); $^{13}$C NMR (100 MHz, CDCl$_3$, 25° C.): δ=15.8 (CH$_3$), 27.7 (SCH$_2$), 38.2 (CH$_2$), 68.5 (CH$_2$OH), 208.1 (C=O); MS (70 eV): m/z (%): 134 (13) [M$^+$], 119 (2) [M$^+$–CH$_3$], 106 (12), 103 (13) [M$^+$–CH$_2$OH], 75 (40) [CH$_3$SCH$_2$CH$_2^+$], 61 (100) [CH$_3$SCH$_2^+$]; Elem. anal.: calcd. for C$_5$H$_{10}$O$_2$S: C, 44.75; H, 7.51; S, 23.89, found: C, 44.77; H, 7.46; S, 24.07; mp 36° C.

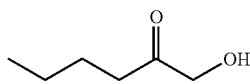

1-Hydroxyhexan-2-one $^1$H NMR (300 MHz, CDCl$_3$, 25° C.): δ=0.85 (t, $^3$J, (H,H)= 7.4 Hz, 3H; CH$_3$), 1.29 (m, $^3$J, (H,H)=7.4 Hz, 2H; 5-CH$_2$), 1.55 (m, $^3$J (H,H)=7.4 Hz, 2H, 4-CH$_2$), 2.35 (t, $^3$J (H,H)=7.4 Hz, 2H, 3-CH$_2$), 3.13 (bs, 1H, OH), 4.18 (s, 2H, CH$_2$OH); $^{13}$C NMR (100 MHz, CDCl$_3$, 25° C.): δ=13.7 (CH$_3$), 22.3 (5-CH$_2$), 25.8 (4-CH$_2$), 38.1 (3-CH$_2$), 68.1 (CH$_2$OH), 209.9 (C=O); MS (70 eV): m/z (%): 116 (4) [M$^+$], 86 (4), 85 (67) [M$^+$–CH$_2$OH], 57 (100) [M$^+$–COCH$_2$OH], 55 (11), 41 (75), 39 (22).

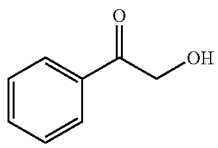

2-Hydroxy-1-phenylethanone (2-Hydroxyacetophenone)

$^1$H NMR (300 MHz, CDCl$_3$, 25° C.): d=4.79 (s, 2H, CH$_2$), 5.6 (bs, 1H; OH), 7.55-7.97 (m, 5H; Ph) ppm; $^{13}$C NMR (100.6 MHz, CDCl$_3$, 25° C.): d=67.7 (CH$_2$), 128.7, 128.8 (x 2), 133.2 (x 2), 136.7, 198.4 (C=O) ppm; MS (70 eV), m/z (%): 136 (6) [M$^+$], 106 (8), 105 (100), [M$^+$–CH$_2$OH], 77 (60) [Ph$^+$], 51 (16).

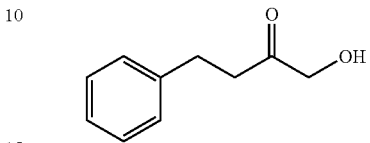

1-Hydroxy-3-phenylpropan-2-one $^1$H NMR (300 MHz, CDCl$_3$, 25° C.): d=2.60 (t, $^3$J, (H,H)= 7.7 Hz, 2H; 4-CH$_2$), 2.84 (t, $^3$J (H,H)=7.7 Hz, 2H; 3-CH$_2$), 3.19 (s, 1H; OH), 4.06 (s, 2H: 1-CH$_2$), 7.05-7.12 (m, 5H; Ph) ppm; $^{13}$C NMR (100.6 MHz, CDCl$_3$, 25° C.): d=29.5 (4-C), 39.9 (3-C), 68.4 (1-C), 126.4, 128.3 (x 2), 128.7 (x 2), 140.3, 209.1 (C=O) ppm; MS (70 eV): m/z (%): 164 (4) [M$^+$], 146 (4), 133 (35) [M$^+$–CH$_2$OH], 105 (73) [M$^+$COCH$_2$OH], 79 (12), 78 (10), 77 (22) [Ph$^+$], 65 (13), 51 (12), 39 (10).

1-Hydroxynonan-2-one $^1$H NMR (300 MHz, CDCl$_3$, 25° C.): δ=0.82 (m, $^3$J, (H,H)= 6.7 Hz, 3H; CH$_3$), 1.20 (m, 8H; 5-8-CH$_2$), 1.56 (m, $^3$J (H,H)=7.4 Hz, 2H, 4-CH$_2$), 2.33 (t, $^3$J (H,H)=7.4 Hz, 2H; 3-CH$_2$), 3.18 (bs, 1H; OH), 4.17 (s, 2H: CH$_2$OH); $^{13}$C NMR (100 MHz, CDCl$_3$, 25° C.): δ=14.0 (CH$_3$), 22.6 (8-CH$_2$), 23.7 (7-CH$_2$), 28.9 (6-CH$_2$), 29.1 (5-CH$_2$), 31.6 (4-CH$_2$), 38.4 (3-CH$_2$), 68.1 (CH$_2$OH), 210.0 (C=O); MS (70 eV): m/z (%): 158 (3) [M$^+$], 127 (22) [M$^+$–CH$_2$OH], 111 (18), 95 (2), 83(8), 69 (100), 57 (68), 55 (47), 43 (48), 41 (43).

1-cyclohexyl-2-hydroxyethanone $^1$H NMR (300 MHz, CDCl$_3$, 25° C.): d=1.1-1.4 (m, 6H, CH$_2$), 1.6-1.8 (m, 4H; CH$_2$), 2.32 (m, $^3$J; (H,H)=11.4, 3.3 Hz, 1H, CH) 3.22 (bs, 1H, OH), 4.23 (s, 2H, CH$_2$OH) ppm; $^{13}$C NMR (100.6 MHz, CDCl$_3$, 25° C.): d=25.4 (x 2), 25.6 (x 2), 47.0 (CH), 66.4 (CH$_2$OH), 212.7 (C=O) ppm; MS (70 eV), m/z (%): 142 (2) [M$^+$], 111 (27) [M$^+$–CH$_2$OH], 84 (7), 83 (100) [M$^+$–COCH$_2$OH], 67 (12), 55 (91), 41 (48), 39 (28).

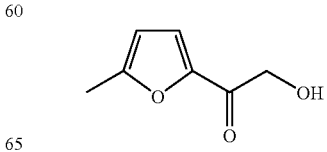

2-Hydroxy-1-(5-methylfuran-2-yl)ethanone $^1$H NMR (300 MHz, CDCl$_3$, 25° C.): d=2.34 (d, $^4$J, (H,H)=1.0, CH$_3$), 3.28 (bs, 1H; OH), 4.67 (s, 2H; CH$_2$), 6.14 (dq, J (H,H)=3.6, 1.0, 1H, 4'-H), 7.14 (d, $^3$J (H,H)=3.6, 1H; 3'-H) ppm; $^{13}$C NMR (100.6 MHz, CDCl$_3$, 25° C.): d=14.0 (CH$_3$), 64.6 (CH$_2$), 109.3 (4'-C), 119.8 (3'-C), 148.7 (5'-C), 158.6 (2'-C), 186.7 (C=O) ppm; MS (70 eV), m/z (%): 140 (20) [M$^+$], 109 (100) [M$^+$-HOCH$_2$], 95 (2), 81 (1), 65 (1), 53 (33), 43 (7).

NMR data of the novel catalyst (H$_2$IMes.CO$_2$)

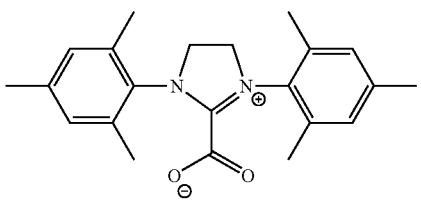

1,3-Dimesityl-4,5-dihydro-1H-imidazol-3-ium-2-carboxylate $^1$H NMR (300 MHz, DMSO-d$_6$, 25° C.): d=2.25 (s, 6H; CH$_3$), 2.36 (s, 12H; CH$_3$), 4.43 (s, 4H; CH$_2$) 6.98 (s, 4H; Arom.) ppm; $^{13}$C NMR (300.6 MHz, DMSO-d$_6$, 25° C.): d=20.5 (4 CH$_3$), 24.1 (2 CH$_3$), 52.8 (2 CH$_2$), 132.5 (C-3', C-5'), 134.7 (C-4'), 139.8 (C-2', C-6'), 142.5 (C-1'), 155.5 (C-2), 167.7 (CO$_2$) ppm.

All references cited herein are fully incorporated by reference in their entirety. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. In a method for the preparation of α-hydroxy ketones by acyloin addition of aldehydes, the improvement comprising catalyzing said addition using a catalyst of formula II or III:

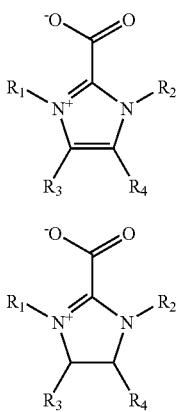

wherein:

R$_1$ and R$_2$ are the same or different and are each a C$_6$-C$_{10}$-aryl, heteroaryl, branched or unbranched, optionally mono- or poly-C$_1$-C$_4$-alkyl- or -heteroalkyl-substituted C$_1$-C$_{10}$-alkyl, C$_3$-C$_6$-cycloalkyl or mono- or poly-C$_1$-C$_4$-alkyl-substituted C$_6$-C$_{10}$-aryl, and R$_3$ and R$_4$ are the same or different and are each hydrogen, branched or unbranched C$_1$-C$_6$-alkyl, C$_3$-C$_6$-cycloalkyl, C$_6$-C$_{10}$-aryl or heteroaryl.

2. A compound of formula IV:

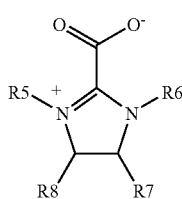

wherein R5 and R6 are the same or different and are each a poly-C$_1$-C$_4$-alkyl-substituted C$_6$-C$_{10}$-aryl, or poly-C$_1$-C$_4$-alkyl-substituted C$_1$-C$_{10}$-alkyl, and R7 and R8 are the same or different and are each a branched or unbranched C$_1$-C$_6$-alkyl.

3. The compound of claim 2, wherein:

a) R5, R6 or both R5 and R6 are mesityl; and
b) R7, R8 or both R7 and R8 are methyl.

4. A process for preparing α-hydroxy ketones of formula I:

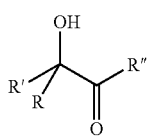

comprising reacting a carbonyl compound of the general formula RR'C=O with a carbonyl compound of the general formula HR''C=O, in the presence of a catalyst of formula II, III or IV:

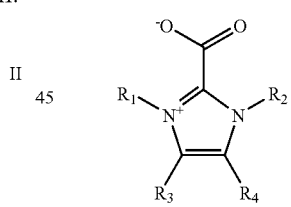

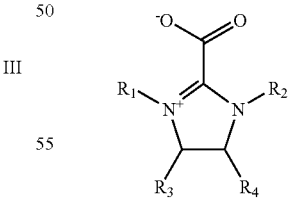

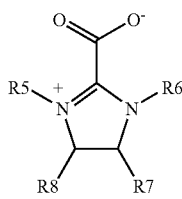

wherein:
R₁ and R₂ are the same or different and are each a $C_6$-$C_{10}$-aryl, heteroaryl, branched or unbranched, optionally mono- or poly-$C_1$-$C_4$-alkyl- or -heteroalkyl-substituted $C_1$-$C_{10}$-alkyl, $C_3$-$C_6$-cycloalkyl or mono- or poly-$C_1$-$C_4$-alkyl-substituted $C_6$-$C_{10}$-aryl,
R₃ and R₄ are the same or different and are each a hydrogen, branched or unbranched $C_1$-$C_6$-alkyl, $C_3$-$C_6$-cycloalkyl, $C_6$-$C_{10}$-aryl or heteroaryl,
R5 and R6 are the same or different and are each a $C_6$-$C_{10}$-aryl, mono- or poly-$C_1$-$C_4$-alkyl-substituted $C_6$-$C_{10}$-aryl, optionally mono- or poly-$C_1$-$C_4$-alkyl-substituted $C_1$-$C_{10}$-alkyl or $C_3$-$C_6$-cycloalkyl,
R7 and R8 are the same or different and are each a hydrogen or branched or unbranched $C_1$-$C_6$-alkyl,
R and R' are the same or different and are each H or a straight-chain or branched and optionally substituted $C_1$-$C_{12}$-alkyl radical; and
R" is $H_3CSCH_2CH_2$, t-butyl, n-butyl, sec-butyl, n-propyl, i-propyl, an optionally heteroatom-substituted $C_6$-$C_{18}$-aryl, heteroaryl, $C_6$-$C_{18}$-arylalkyl, or heteroalkyl.

5. The process of claim 4, wherein R" is phenylmethyl, and wherein said phenyl may be heteroatom-substituted.

6. The process of claim 4, wherein said catalyst is a compound of formula IV, wherein:
R5 and R6 are the same or different and are each $C_6$-$C_{10}$-aryl, mono- or poly-$C_1$-$C_4$-alkyl-substituted $C_6$-$C_{10}$-aryl, optionally mono- or poly-$C_1$-$C_4$-alkyl-substituted $C_1$-$C_{10}$-alkyl or $C_3$-$C_6$-cycloalkyl,
R7 and R8 are the same or different and are each a branched or unbranched $C_1$-$C_6$-alkyl, and
with the proviso that, when R7 and R8 are each hydrogen, R5 and R6 are not both phenyl.

7. The process of claim 4, wherein R and R' are both H and R" is $CH_3SCH_2CH_2$.

8. The process of claim 4, wherein:
R is H,
R' a straight-chain or branched and optionally substituted $CH_1C_{12}$-alkyl radical and
R" is $CH_3SCH_2CH_2$.

9. The process of claim 4, wherein:
R is H,
R' is $CH_3$ and
R" is $CH_3SCH_2CH_2$.

10. The process of claim 4, wherein:
R is H,
R' is $C_2H_5$ and
R" is $CH_3SCH_2CH_2$.

11. The process of claim 4, wherein said catalyst is used at a concentration of 0.1-5 mol % based on the aldehyde.

12. The process of claim 11, wherein said process is performed at a temperature of −20° C. to 100° C.

13. The process of claim 11, wherein said process is performed at a temperature of 15° C. to 80° C.

14. The process of claim 13, wherein said process is performed under a partial pressure of 0.1-20 bar of carbon dioxide.

15. A compound of formula VI, formula VII or formula VIII:

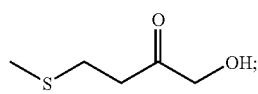

(VI)

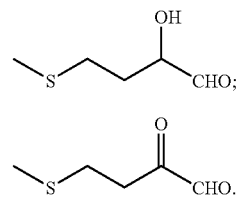

(VII)

(VIII)

16. A process for preparing a catalyst of formula II, III or IV:

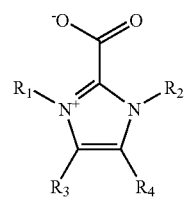

II

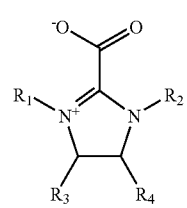

III

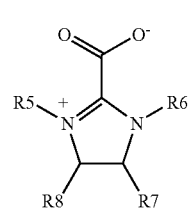

(IV)

wherein:
R₁ and R₂ are the same or different and are each a $C_6$-$C_{10}$-aryl, heteroaryl, branched or unbranched, optionally mono- or poly-$C_1$-$C_4$-alkyl- or -heteroalkyl-substituted $C_1$-$C_{10}$-alkyl, $C_3$-$C_6$-cycloalkyl or mono- or poly-$C_1$-$C_4$-alkyl-substituted $C_6$-$C_{10}$-aryl,
R₃ and R₄ are the same or different and are each hydrogen, branched or unbranched $C_1$-$C_6$-alkyl, $C_3$-$C_6$-cycloalkyl, $C_6$-$C_{10}$-aryl or heteroaryl;
R5 and R6 are the same or different and are each a poly-$C_1$-$C_4$-alkyl-substituted $C_6$-$C_{10}$-aryl, or poly-$C_1$-$C_4$-alkyl-substituted $C_1$-$C_{10}$-alkyl; and
R7 and R8 are the same or different and are each a branched or unbranched $C_1$-$C_6$-alkyl;
said process comprising, reacting a compound of formula IX, X or XI:

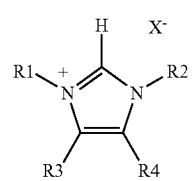

IX

-continued

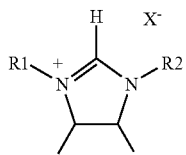

X

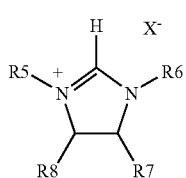

XI with CO₂ in the presence of a base,
and wherein X is Cl, Br, I, pCH₃C₆H₄SO₃, BF₄, PF₆, or CH₃SO₃.

17. The process of claim 16, wherein said base has a corresponding acid with a pKa greater than 8.

18. The process of claim 17, wherein said base is an alkali metal or alkaline earth metal carboxylate, alkali metal or alkaline earth metal alkoxide, alkali metal or alkaline earth metal carbonate or a primary, secondary, or tertiary amine or bicyclic amine.

19. The process of claim 17, wherein said base is sodium acetate, potassium tert-butoxide, or 1,8-diazabicyclo [5.4.0] undec-7-ene (DBU).

20. The process of claim 16, wherein said process is performed at temperatures of 15 to 80° C.

\* \* \* \* \*